US00PP11586P

United States Patent [19]

Boeder

[11] Patent Number: Plant 11,586

[45] Date of Patent: Oct. 24, 2000

[54] CHRYSANTHEMUM PLANT NAMED 'LORIKEET'

[75] Inventor: Mark Boeder, West Sussex, United Kingdom

[73] Assignee: Cleangro Limited, West Sussex, United Kingdom

[21] Appl. No.: 09/038,792

[22] Filed: Mar. 11, 1998

[51] Int. Cl.[7] ..... A01H 5/00

[52] U.S. Cl. ..... Plt./287

[58] Field of Search ..... Plt./287, 293, 292

[56] References Cited

U.S. PATENT DOCUMENTS

| | | | |
|---|---|---|---|
| P.P. 9,584 | 6/1996 | Fuess | Plt./287 |
| P.P. 10,212 | 1/1998 | Wain | Plt./287 |

*Primary Examiner*—Howard J. Locker
*Attorney, Agent, or Firm*—Christie, Parker & Hale, LLP

[57] ABSTRACT

A new plant variety of Chrysanthemum producing dark lavender to red-purple flowers.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Lorikeet'.

The female parent of the new variety is the variety known as 'Lynn' (U.S. Plant Pat. No. 8,171) and the male parent is an undistributed, unnamed seedling identified as 'G77-C3'. The new variety has been asexually reproduced by vegetative cuttings in Ventura County, Calif. and the distinguishing characteristics are retained through successive generations of asexual reproduction.

SUMMARY OF THE INVENTION

'Lorikeet' is a pot type Chrysanthemum plant variety that produces dark lavender to red purple flowers.

Comparison With 'Lynn'

'Lorikeet' differs from the female parent in producing a more compact plant with smaller and more numerous lavender purple flowers in contrast to very light pink flowers of 'Lynn'.

BRIEF DESCRIPTION OF ILLUSTRATIONS

The accompanying photographs show typical specimens of the new variety with colors being as nearly true as possible with illustrations of this type.

DESCRIPTION OF THE PLANT

Figure 1:
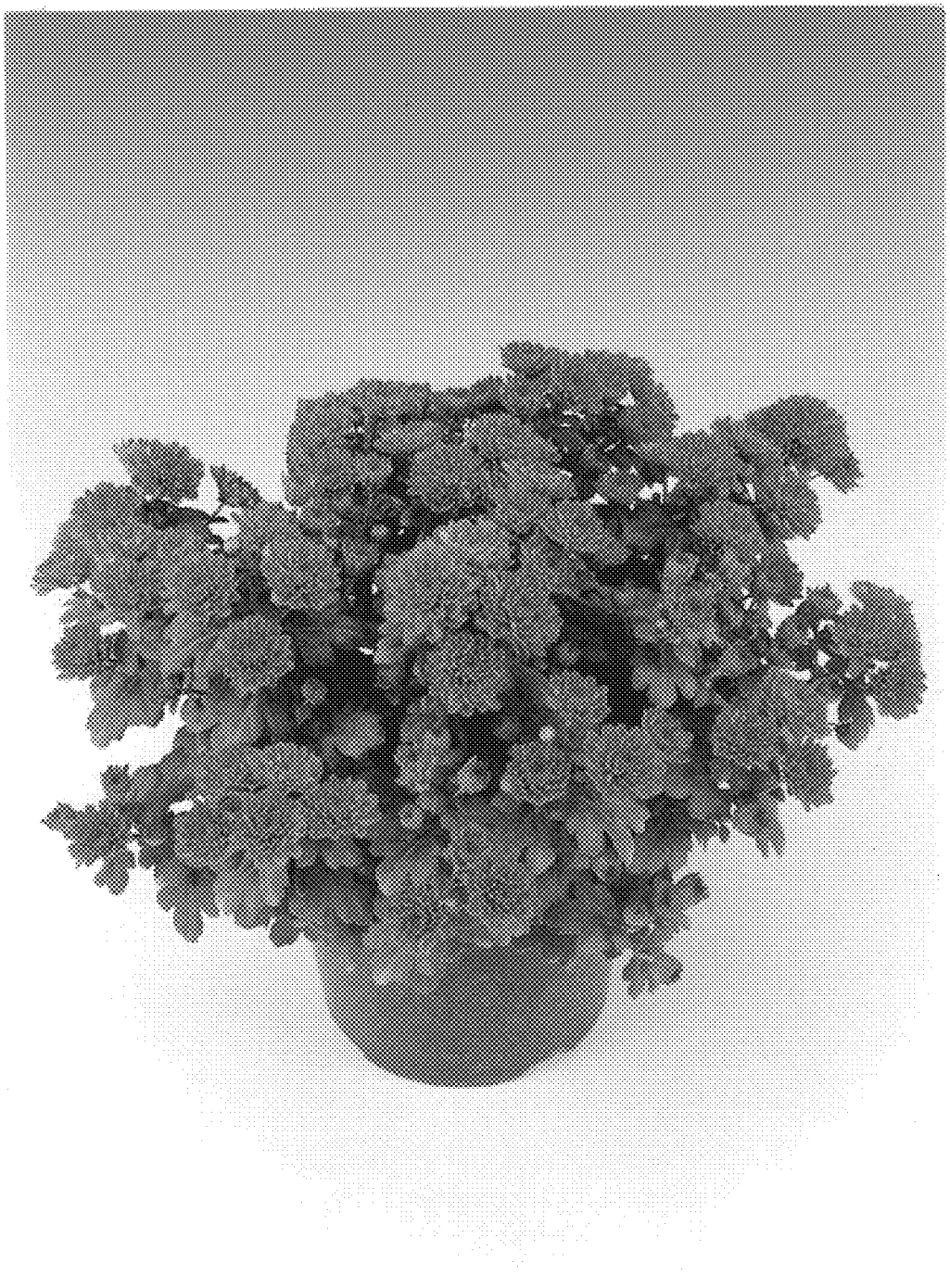
FIG. 1 is a whole plant view of the new cultivar grown in a pot.
Figure 2:
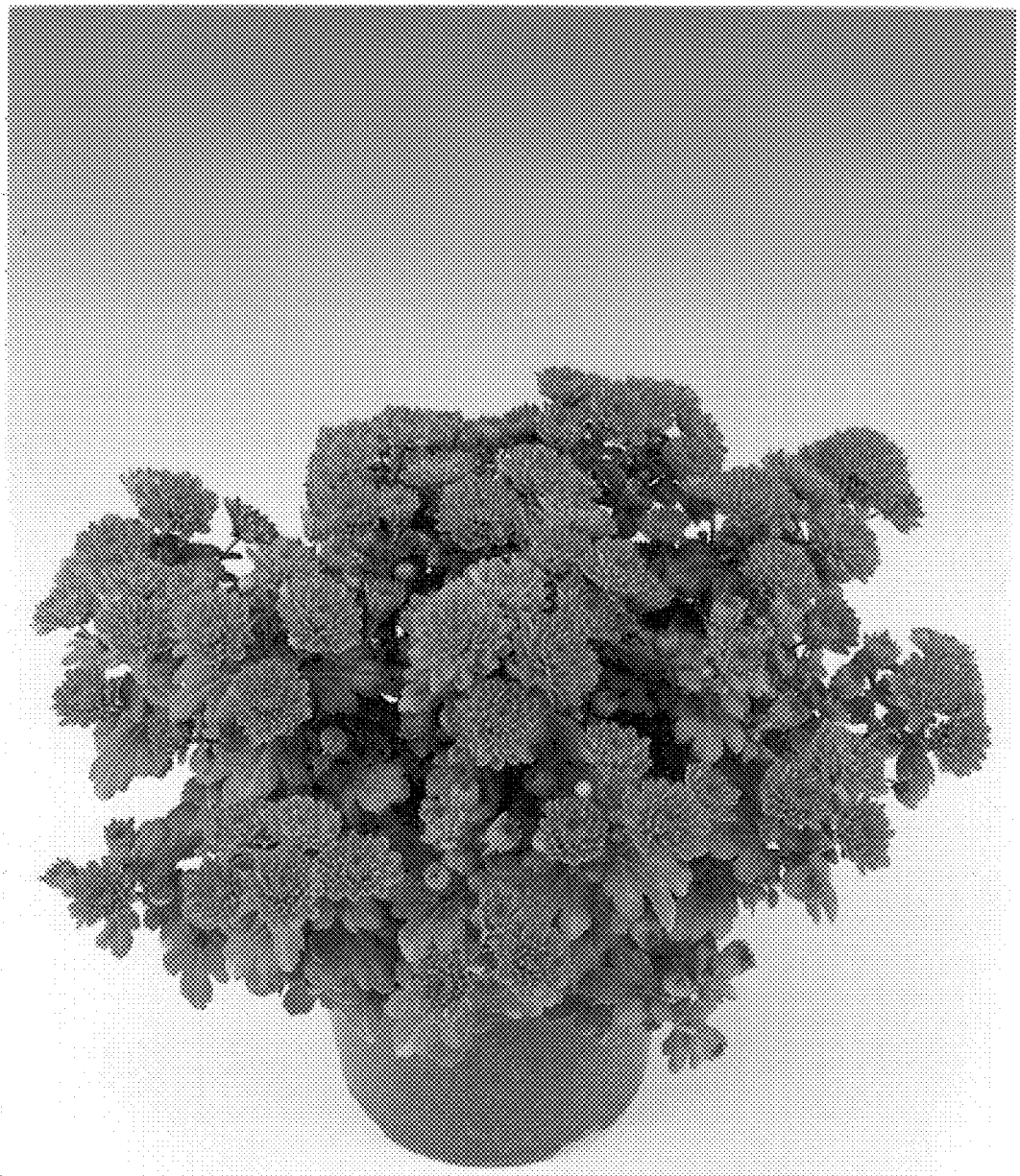
FIG. 2 is a closer view, showing inflorescence and foliage characteristics of the new cultivar in greater detail.

The following description of the new variety is of specimens grown in a greenhouse in Ventura County, Calif. in the month of October, 'Lorikeet' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 3 to 4 breaks per pinch. It has been observed that the shelf life of 'Lorikeet' is about 19–22 days with the response time of about 6.5 weeks. No treatment with growth retardant is required. Useful growing conditions include night temperatures of about 64°–66° F., day temperatures of about 80°–85° F. and about 5,000 foot-candles of light.

Plant:

*Habit.*—Short, compact, mounding.
*Height.*—About 16 cm.
*Number of breaks from pinch.*—About 3 to 4.
*Typical container sizes commercially grown in.*—4", 6", 1 gallon pots.
*Length of lateral branches.*—About 8 cm.
*Stem Color.*—Near 144A.

Foliage:

*Leaf arrangement.*—Alternate.
*Number of leaves per lateral branch.*—About 12 fully expanded leaves.
*Leaf size.*—Length: About 4.3 cm. Width: About 3.8 cm.
*Leaf shape.*—Ovate.
*Attachment.*—Petioled.
*Leaf apex.*—Obtuse.
*Base.*—Truncate.
*Margin.*—Serrate, palmately lobed.
*Aspect.*—Very slight down curve.
*Surface.*—Top: Lightly pubescent. Bottom: Pubescent.
*Petiole Length.*—About 0.7 cm.
*Stipules.*—Not present.
*Color.*—Mature leaf: Top: Near 147A. Bottom: Near 137B. Young leaf: Top: Near 137A. Bottom: Near 137B.

Flower:

*Inflorescence form.*—Cyme.
*Flower form.*—Decorative.
*Number of blooms per branch.*—About 10.
*Diameter of fully expanded bloom.*—About 3.5 cm.
*Depth of fully expanded bloom.*—About 1.5 cm.
*Longevity of bloom.*—About 19–22 days.
*Sepal number.*—About 35.
*Color.*—Near 137A.
*General appearance of sepals.*—Thick and tightly held; very little membrane.
*Peduncle length.*—About 2.5 cm. Habit: Sharply angled. Surface: Highly pubescent. Strength: Very sturdy.
*Flower bud.*—Diameter: About 0.7 cm. Height: About 0.4 cm.

*Ray florets.*—Number per flower: About 140 . Shape: Oblanceolate. Apex: Obtuse, 3 lobed. Base: Tapered. Margin: Entire. Aspect: Curved up. Length: About 1.6 cm. Width: About 0.6 cm.

*Disc florets.*—Number per flower: About 2. Shape: Tubular. Length: About 0.3 cm. Width: About 0.08 cm.

*Fragrance.*—None.

Flower color:

*General flower description.*—Dark lavender to red-purple decorative; very flat flower form with evenly radiating ray florets.

*Ray florets, top side.*—Immature: Near 74 B. Mature: Near 74C. Fading: Near 74D.

*Ray floret, under side.*—Immature: Near 70A. Mature: Near 74C. Fading: Near 70C.

*Disc florets.*—Mature: Near 12A.

*Changes as the flower ages.*—Outermost ray florets fading with age, flower from remains flat; flower eventually turns brown and dry on the plant.

Reproductive Organs:

*Ray Florets.*—Pistillate. Stigma shape: Branched, curled. Stigma color: Near 8A. Style length: About 0.3 cm.

*Disc Florests: Stigma shape: Linear. Style Length: About* 0.15 cm. Stamen number: About 6 . Anther length: About 0.1 cm. Pollen color: Near 16A. Pollen quantity: Moderate in individual disc florets.

What is claimed is:

1. A new and distinct Chrysanthemum plant of the variety substantially as herein shown and described.

* * * * *